United States Patent [19]

Raj et al.

[11] 4,308,255

[45] Dec. 29, 1981

[54] BALANCED ONCOTIC PRESSURE FLUID

[75] Inventors: Ghen M. G. Raj, Wilton; Charles L. Fox, Jr., Sherman, both of Conn.

[73] Assignee: Haemophor Corporation, Wilton, Conn.

[21] Appl. No.: 133,517

[22] Filed: Mar. 24, 1980

[51] Int. Cl.³ .................... A61K 31/06; A61K 31/14; A61K 31/70; A61K 31/315

[52] U.S. Cl. ................................. 424/153; 424/127; 424/154; 424/156; 424/180; 424/289

[58] Field of Search ............... 424/127, 153, 289, 154, 424/180, 156

[56] References Cited

PUBLICATIONS

Chem. Abst., vol. 89 (1978), 48915s.
Physicians' Desk Reference, Quarterly Supplement No. 3, Jul. 1966, p. 31.
Pharmacia, Rheomacrodex (Dextran 40) flow improver, 1968.
J. Jirka & E. Kotkova, Peritoneal Dialysis by Iso-Oncotic Dextran Solution in Anaesthetized Dogs, Intra-Peritoneal Fluid Volume and Protein Concentration in the Irrigation Fluid, 1967, Dialysis and Renal Transplantation. Proc. 4th Conf. (147–145).
Dr. John Bergan, Thrombosis, Symposium, Contemporary Surgery, vol. 14, May 1979 (pp. 80–101).
Alan T. Marty, M.D., & Benjamin W. Zweifach, The High Oncotic Pressure Effects of Dextrans, Arch Surg. vol. 101, Sep. 1970 (pp. 421–424).
Sven-Erik Bergentz, M.D., On bleeding and Clotting Problems in Post-Traumatic States, Critical Care Medicine, 1976, pp. 41–45.
W. C. Shoemaker, M.D., Choice of Replacement Fluids in Shock, Hospital Physician 7/77 (pp. 27–31).
Martin S. Litwin, MD, Blood viscosity changes after trauma, Critical Care Medicine, Mar.–Apr. 1976 (pp. 67–70).
Sidney Vernon, MD, The Ideal Initial Infusion in Unexpected Shock, Surgery, October 1970, Vol. 131, 748–749.
N. Mendler & R. Schrock, Osmotic Properties of Macromolecular Solutions and Gels—Physical Aspects and Physiological Relevance, Int. Symp. Rottach-Egern 1971, pp. 105–117.
Lars Garby & Gunnar Grotte, Theoretical Considerations on the "Colloid Osmotic Effect" of Plasma Expanders, Acta Societatis Medicorum Upsaliensis, Vol. IXI, Nos. 1–2, 1956 (pp. 103–106).
John J. Mulcahy & Richard L. Malvin, The Effective Oncotic Pressure of Dextran, Vox Sang 29: 237–241 (1975).
Jon Gjessing, The Use of Dextran as a Dialysing Fluid in Peritonea Dialysis, Acta Med Scand Vol. 185, pp. 237–239, 1969.

Primary Examiner—Stanley J. Friedman
Attorney, Agent, or Firm—Thaddius J. Carvis

[57] ABSTRACT

A balanced oncotic pressure fluid suitable as a dialysate in the treatment of patients suffering from loss of kidney function. The solution comprises on the basis of 1 liter of solution about 200–300 mEq sodium, about 145–215 mEq chloride, about 55–85 mEq bicarbonate or acetate or lactate, and about 2–10% by weight dextran, the ratio of sodium to chloride being about 1.4:1. An example of the above solution contains about 224 mEq sodium, about 164 mEq chloride, about 72 mEq acetate, about 6% by weight dextran, about 2% dextrose, about 7 mg zinc gluconate, about 2 mEq potassium, about 3 mEq calcium, and about 2 mEq magnesium.

6 Claims, No Drawings

BALANCED ONCOTIC PRESSURE FLUID

BACKGROUND OF THE INVENTION

This invention relates to solutions suitable as the dialysate in both hemodialysis and peritoneal dialysis of persons suffering from kidney failure.

U.S. Pat. No. 3,993,750, issued to Fox, one of the present inventors, discloses improved resuscitation solutions for the treatment of trauma in humans. The hypertonic solutions of this patent comprise on the basis of 1 liter of solution about 200-300 mEq sodium, about 145-215 mEq chloride, and about 55-85 mEq bicarbonate or acetate or lactate, the sodium to chloride ratio being about 1.4 to 1. Optional ingredients which may be added to the solution include about 1.5-2.5 mEq magnesium, about 3.5-5.5 mEq potassium, up to about 5.5 mEq calcium, about 2.5-3.5 mEq phosphate, and up to about 5% by weight dextrose. These solutions provide the advantages of replacing lost sodium, reducing total water intake and edema, and simulating the sodium to chloride ratio and the electrolyte values of normal blood.

Many of the same considerations involved in formulating a balanced salt solution for treating trauma are also involved in formulating a balanced salt solution for treating kidney failure. In healthy individuals, the sodium content of the body, and hence extracellular volume, is determined by renal excretion of sodium. When the kidneys fail, the patient must be treated by kidney transplant, or else by hemodialysis or peritoneal dialysis.

In hemodialysis, electrolyte and fluid imbalances are corrected by pumping the patient's blood through a device containing a semi-permeable membrane. Water, electrolytes, toxic substances and metabolites in the blood diffuse through the membrane into a solution of salts known as the dialysate. The toxic substances and metabolites are then washed away in the dialysate and the electrolyte values of the blood are restored to normal.

In peritoneal dialysis, a similar dialysate solution is pumped into the peritoneal cavity and surrounds the gut. The same process of diffusion and osmosis of water and toxic substances from the blood takes place through the wall of the gut into the dialysate. Electrolyte values are restored and the toxic substances are washed away in the dialysate.

Because crystalloids diffuse in both directions across the membrane, any electrolyte abnormality in the patient's blood will be corrected by the use of a solution containing normal concentrations of the important electrolytes. Desirably, the dialysate used for hemodialysis and for peritoneal dialysis simulates normal electrolyte values.

Examples of dialysates currently available are the Dianeal solutions sold by Travenol Laboratories, Deerfield, Illinois, which are described in the brochure "Dianeal (Peritoneal Dialysis Solution)" (June 1977).

SUMMARY AND DETAILED DESCRIPTION OF THE INVENTION

The present invention provides an improved hypertonic solution suitable for use as a dialysate for the hemodialysis and for the peritoneal dialysis of patients suffering from loss of kidney function. The balanced oncotic pressure fluid comprises on the basis of 1 liter of solution about 200-300 mEq of sodium, about 145-215 mEq of chloride, about 55-85 mEq of bicarbonate or acetate or lactate, and about 2-10% dextran, the sodium to chloride ratio being about 1.4:1. Desirably, a hypertonic solution in accordance with this invention, in addition to the above-indicated composition, also includes about 1.5-2.5 mEq of magnesium, about 1-5.5 mEq of potassium and up to about 5.5 mEq of calcium. Desirably, a solution in accordance with this invention also includes up to about 5% by weight dextrose. The solution may also contain up to about 15 mg of zinc gluconate as an additive. The hypertonic solutions in accordance with this invention tend to be alkaline, i.e., a pH greater than 7.0. Desirably, the pH of the solutions are adjusted by the addition of acids or bases to a more suitable value.

An example of a hypertonic solution according to the present invention would be a solution containing about 224 mEq sodium, about 164 mEq chloride, about 72 mEq acetate, about 2 mEq potassium, about 3 mEq calcium, about 2 mEq magnesium, about 6% dextran, about 2% dextrose and about 7.1 mg zinc gluconate. The ratio of sodium to chloride in this solution is about 1.37:1.

Normal plasma on a per liter basis contains 140 mEq sodium, about 103 mEq chloride, about 27 mEq bicarbonate, about 5 mEq calcium, about 5 mEq potassium and about 3 mEq magnesium. The sodium to chloride ratio of normal plasma is about 1.4, substantially the same as in the above solution. The solutions of the present invention are hypertonic to normal plasma which is about 280 mOsm per liter, the above example being 585 mOsm per liter.

Dextran is a water-soluble polysaccharide of dextrose. It is used to extend the volume of plasma and to reduce blood viscosity. Any convenient dextran, such as dextran 40, a low molecular weight dextran, may be used in preparing solutions of the present invention, but an iso-oncotic substance such as dextran 70, hydroxyethylstarch, or gelatin of M.W. approximately 60,000 would be preferable.

The solutions of the present invention may be prepared by adding to the water the necessary amounts of water-soluble salts which yield the cations and anions of the solutions. Suitable water-soluble salts include NaCl, KCl, NaHCO$_3$, KHCO$_3$, Na$_2$SO$_4$, MgCl$_2$, Na acetate, K acetate, Na lactate, K lactate, CaCl$_2$ and MgSO$_4$. Zinc in the form of zinc gluconate could be added to avoid zinc depletion. For stability purposes, it is usually desirable to use lactate or acetate rather than bicarbonate since bicarbonate would be obtained by metabolism of the lactate or acetate upon administration of the solution. Any desired or necessary adjustment of pH can be obtained by the addition of suitable acids or bases, such as HCl, H$_2$CO$_3$, NaOH, KOH and CO$_2$.

The ingredients of the present solutions can be formed into dry compositions, e.g., as a simple admixture, so that when a sufficient amount of water is added, there would be produced a hypertonic solution having the composition in accordance with this invention.

In peritoneal dialysis, the solutions may be administered to adults in typical dosages of 2 liters per hour. In hemodialysis, the solutions may be administered through conventional dialyzers, or through the compact dialyzer described in patent application Ser. No. 886,458, filed Mar. 14, 1978, by one of the present inventors (Raj). Flow rates of about 150 ml/min are typical for the compact dialyzer. In all cases, solutions according to the present invention gave improved results, reducing the length of time for the procedures because their hypertonicity draws in water containing urea, etc., more rapidly than isotonic solutions now in use.

While the invention has been described with reference to specific embodiments, these references were for purposes of illustration only. Many variations will be readily apparent to those skilled in the art without departing from the spirit and scope of the present invention.

We claim:

1. A method of treating a human suffering from loss of kidney function which comprises administering to said human by hemodialysis, an effective amount of a solution comprising, on the basis of 1 liter of solution, about 200–300 mEq sodium, about 145–215 mEq chloride, about 55–85 mEq bicarbonate or acetate or lactate, and about 2–10% by weight dextran, the ratio of sodium to chloride being about 1.4:1.

2. A method of treating a human suffering from loss of kidney function which comprises administering to said human by peritoneal dialysis, an effective amount of a solution comprising, on the basis of 1 liter of solution, about 200–300 mEq sodium, about 145–215 mEq chloride, about 55–85 mEq bicarbonate or acetate or lactate, and about 2–10% by weight dextran, the ratio of sodium to chloride being 1.4:1.

3. A method of treating a human suffering from loss of kidney function which comprises administering to said human by hemodialysis an effective amount of a solution comprising, on the basis of 1 liter of solution, about 200–300 mEq sodium, about 145–215 mEq chloride, about 55–85 mEq bicarbonate or acetate or lactate, about 2–10% by weight dextran, up to about 5% by weight dextrose, up to about 15 mg of zinc gluconate, about 1.5–2.5 mEq magnesium, about 1–5.5 mEq potassium, and up to about 5.5 mEq calcium, the sodium to chloride ratio being about 1.4:1.

4. A method of treating a human suffering from loss of kidney function which comprises administering to said human by peritoneal dialysis an effective amount of a solution comprising, on the basis of 1 liter of solution, about 200–300 mEq sodium, about 145–215 mEq chloride, about 55–85 mEq bicarbonate or acetate or lactate, about 2–10% by weight dextran, up to about 5% by weight dextrose, up to about 15 mg of zinc gluconate, about 1.5–2.5 mEq magnesium, about 1–5.5 mEq potassium, and up to about 5.5 mEq calcium, the sodium to chloride ratio being about 1.4:1.

5. A method according to claim 3 wherein the solution contains about 224 mEq sodium, about 164 mEq chloride, about 72 mEq acetate, about 6% by weight dextran, about 2% by weight dextrose, about 7 mg zinc gluconate, about 2 mEq magnesium, about 2 mEq potassium, and about 3 mEq calcium.

6. A method according to claim 4 wherein the solution contains about 224 mEq sodium, about 164 mEq chloride, about 72 mEq acetate, about 6% by weight dextran, about 2% by weight dextrose, about 7 mg zinc gluconate, about 2 mEq magnesium, about 2 mEq potassium, and about 3 mEq calcium.

* * * * *